United States Patent
Chavarria et al.

(10) Patent No.: US 11,013,519 B2
(45) Date of Patent: May 25, 2021

(54) ORTHOPAEDIC SURGICAL INSTRUMENT FOR MANIPULATING A MEDICAL DEVICE

(71) Applicant: DePuy Synthes Products, Inc., Raynham, MA (US)

(72) Inventors: Jason M. Chavarria, Leesburg, IN (US); Jeremiah M. Lewis, Leesburg, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 140 days.

(21) Appl. No.: 16/201,122

(22) Filed: Nov. 27, 2018

(65) Prior Publication Data

US 2020/0163681 A1 May 28, 2020

(51) Int. Cl.
*A61B 17/16* (2006.01)
*A61B 17/56* (2006.01)
*A61B 17/00* (2006.01)

(52) U.S. Cl.
CPC ........ *A61B 17/162* (2013.01); *A61B 17/1624* (2013.01); *A61B 17/1631* (2013.01); *A61B 2017/00473* (2013.01); *A61B 2017/564* (2013.01)

(58) Field of Classification Search
CPC ... A61B 17/16; A61B 17/162; A61B 17/1624; A61B 17/1631; A61B 17/1633; A61B 17/56; A61B 2017/564; A61F 2/46; A61F 2/4603; A61F 2002/4625; A61F 2002/4627; B25B 23/0021; B25B 23/0035; B25G 3/18; B25G 3/26
See application file for complete search history.

(56) References Cited

U.S. PATENT DOCUMENTS

| | | | | |
|---|---|---|---|---|
| 6,059,829 A | * | 5/2000 | Schlapfer | A61F 2/4601 623/17.16 |
| 6,767,366 B2 | * | 7/2004 | Lee | A61F 2/4611 623/17.16 |
| 6,767,367 B1 | * | 7/2004 | Michelson | A61F 2/447 623/17.16 |
| 8,382,840 B2 | * | 2/2013 | Hestad | A61F 2/4611 623/17.16 |
| 9,198,777 B2 | * | 12/2015 | Kraus | A61F 2/4455 |
| 9,339,395 B2 | * | 5/2016 | Prado | A61F 2/4455 |
| 2007/0213737 A1 | * | 9/2007 | Schermerhorn | A61F 2/4465 606/86 R |
| 2017/0056194 A1 | * | 3/2017 | Biedermann | A61F 2/442 |

* cited by examiner

*Primary Examiner* — Larry E Waggle, Jr.
(74) *Attorney, Agent, or Firm* — Barnes & Thornburg LLP

(57) ABSTRACT

An orthopaedic surgical instrument including a shaft including a head sized to be received in the socket of a medical device is disclosed. The orthopaedic surgical instrument includes a retaining flange that is rotatable relative to the head about an axis between a first position in which a tip of the retaining flange is aligned with the head and a second position in which the tip of the retaining flange is received in one of a number of apertures of the medical device when the head of the shaft is received in the socket of the medical device. A system and method including the orthopaedic surgical instrument are also disclosed.

13 Claims, 7 Drawing Sheets

ORTHOPAEDIC SURGICAL INSTRUMENT FOR MANIPULATING A MEDICAL DEVICE

TECHNICAL FIELD

The present disclosure relates generally to orthopaedic surgical instruments and, more particularly, to instruments for operation with a medical device.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, and/or other surgical instruments. An orthopaedic surgical instrument may be used to manipulate a medical device relative to the patient's bone including, for example, to remove the medical device from the patient's bone, or, in conjunction with a surgical drill, to rotate the medical device to advance it into (or out of) the patient's bone.

SUMMARY

According to one aspect of the disclosure, an orthopaedic surgical instrument includes a shaft extending from a first longitudinal end including a head sized to be received in a socket of a medical device and a second longitudinal end including a shank configured to be coupled to a medical instrument. A retaining flange is coupled to the head. The retaining flange is rotatable relative to the head of the shaft between a first position in which a tip of the retaining flange is aligned with the head and a second position in which the tip of the retaining flange extends beyond the head to engage the medical device when the head of the shaft is received in the socket of the medical device. A handle is configured to be operated by a user to rotate the retaining flange between the first position and the second position.

In some embodiments, the head may have a distal edge. The tip of the retaining flange may have a section that is sized and shaped to match the distal edge of the head. The distal edge of the head may have a first corner. The tip section may be sized and shaped to match the first corner of the head. The tip section may be aligned with the first corner when the retaining flange is in the first position.

In some embodiments, the tip of the retaining flange may be a first tip. The retaining flange may have a second tip that, when the retaining flange is in the first position, may be aligned with the head, and, when the retaining flange is in the second position, may extend beyond the head. The retaining flange may have an outer wall. The first tip may have a first pair of segments of the outer wall. Each segment of the first pair of segments may extend along a substantially straight line. The second tip may have a second pair of segments of the outer wall. Each segment of the second pair of segments may extend along a substantially straight line. The outer wall may have a pair of curved segments that connect the first pair of segments to the second pair of segments. The head of the shaft may have a square cross-section.

In some embodiments, an inner shaft may have a first end positioned adjacent to the first longitudinal end of the shaft and a second end positioned in a cavity defined in the shaft. The retaining flange may be coupled to the second end of the inner shaft. The handle may be coupled to the first end of the inner shaft. The inner shaft may be configured to be twisted about a longitudinal axis extending the first end and the second end to apply a torsion force from the retaining flange to a side wall of the socket.

In some embodiments, a locking mechanism may be provided to lock the retaining flange in the second position. The locking mechanism may have an elongated slot defined in the shaft.

According to another aspect of the disclosure, an orthopaedic surgical system includes a medical device configured to be inserted into a patient's bone. The medical device includes a socket positioned to be accessible to a user when the medical device is positioned in the patient's bone. A number of apertures are connected to the socket. An orthopaedic surgical instrument includes a shaft including a head sized to be received in the socket of the medical device. A retaining flange is coupled to the head. The retaining flange is rotatable relative to the head about an axis between a first position in which a tip of the retaining flange is aligned with the head and a second position in which the tip of the retaining flange is received in one of the number of apertures of the medical device when the head of the shaft is received in the socket of the medical device. A handle is configured to be operated by the user to rotate the retaining flange between the first position and the second position.

In some embodiments, the head may have a distal edge. The tip of the retaining flange may have a section that is sized and shaped to match the distal edge of the head such that, when the retaining flange is positioned in the first position, the head and the retaining flange may be advanced into the socket of the medical device. When the orthopaedic surgical instrument is viewed in a plane extending orthogonal to the axis, the distal edge of the head may have an edge section that extends along a substantially straight line. When the retaining flange is positioned in the first position, the tip of the retaining flange may extend beyond the edge section.

In some embodiments, the tip of the retaining flange is a first tip. The retaining flange may have a second tip that, when the retaining flange is in the first position, may be aligned with the head, and, when the retaining flange is in the second position, may be received in another aperture of the number of apertures of the medical device when the head of the shaft is received in the socket of the medical device.

In some embodiments, the shaft may have a shank configured to be coupled to a rotary surgical tool.

According to yet another aspect of the disclosure, a method of performing an orthopaedic surgical procedure includes aligning a head of an orthopaedic surgical instrument with a socket of a medical device. The head of the orthopaedic surgical instrument is advanced into the socket of the medical device. A retaining flange is rotated relative to the head while keeping the head stationary to advance the retaining flange into an aperture of the medical device. The aperture is connected to the socket.

In some embodiments, the orthopaedic surgical instrument may extend along a longitudinal axis. Rotating the retaining flange may require rotating the retaining flange about the longitudinal axis.

In some embodiments, the aperture may be positioned radially outward from the socket of the medical device.

In some embodiments, a rotary surgical tool may be attached to a shank of the orthopaedic surgical instrument. The rotary surgical tool may be operated to rotate the orthopaedic surgical instrument and the medical device about the longitudinal axis.

In some embodiments, the method includes twisting an inner shaft coupled to the retaining flange to apply a torsion force from the retaining flange to a side wall of the aperture.

BRIEF DESCRIPTION OF THE DRAWINGS

The detailed description particularly refers to the following figures, in which.

DETAILED DESCRIPTION OF THE DRAWINGS

Figure 1:
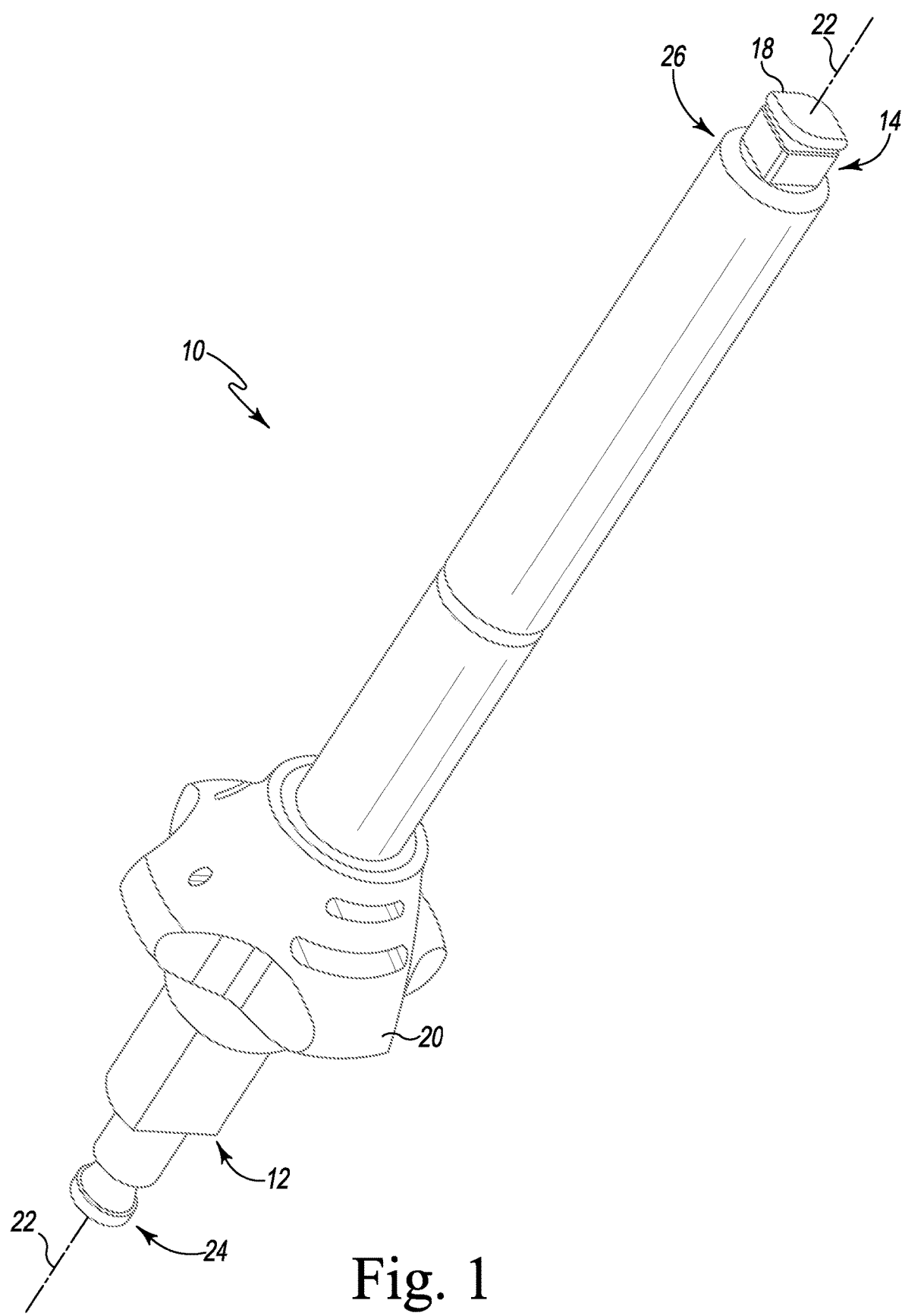
FIG. 1 is a perspective view of an orthopaedic surgical instrument for use with a medical device.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic surgical instrument 10 is shown. The orthopaedic surgical instrument 10 includes a shank 12 configured to be coupled to a medical instrument such as, for example, a surgical drill (not shown) and a head 14 configured to be coupled to a medical device 16 (see FIG. 6). The orthopaedic surgical instrument 10 also includes a retaining flange 18 that is configured to rotate relative to the head 14 to selectively engage the medical device 16 to secure the medical device to the orthopaedic surgical instrument 10. A handle 20 is included in the instrument 10 to rotate the retaining flange 18. As described in greater detail below, the orthopaedic surgical instrument 10 may be used to manipulate the medical device 16 relative to the patient's bone including, for example, to remove the medical device 16 from the patient's bone, or, in conjunction with a surgical drill, to rotate the medical device 16 to advance it into (or out of) the patient's bone.

The orthopaedic surgical instrument 10 extends along a longitudinal axis 22 from a distal end 24 to a proximal end 26. In the illustrative embodiment, the shank 12 is positioned at the distal end 24 and the retaining flange 18 is positioned at the opposite proximal end 26. The retaining flange 18 is configured to rotate about the axis 22 between the disengaged position shown in FIGS. 1 and 4 and the engagement position shown in FIG. 5, as described in greater detail below.

Figure 2:
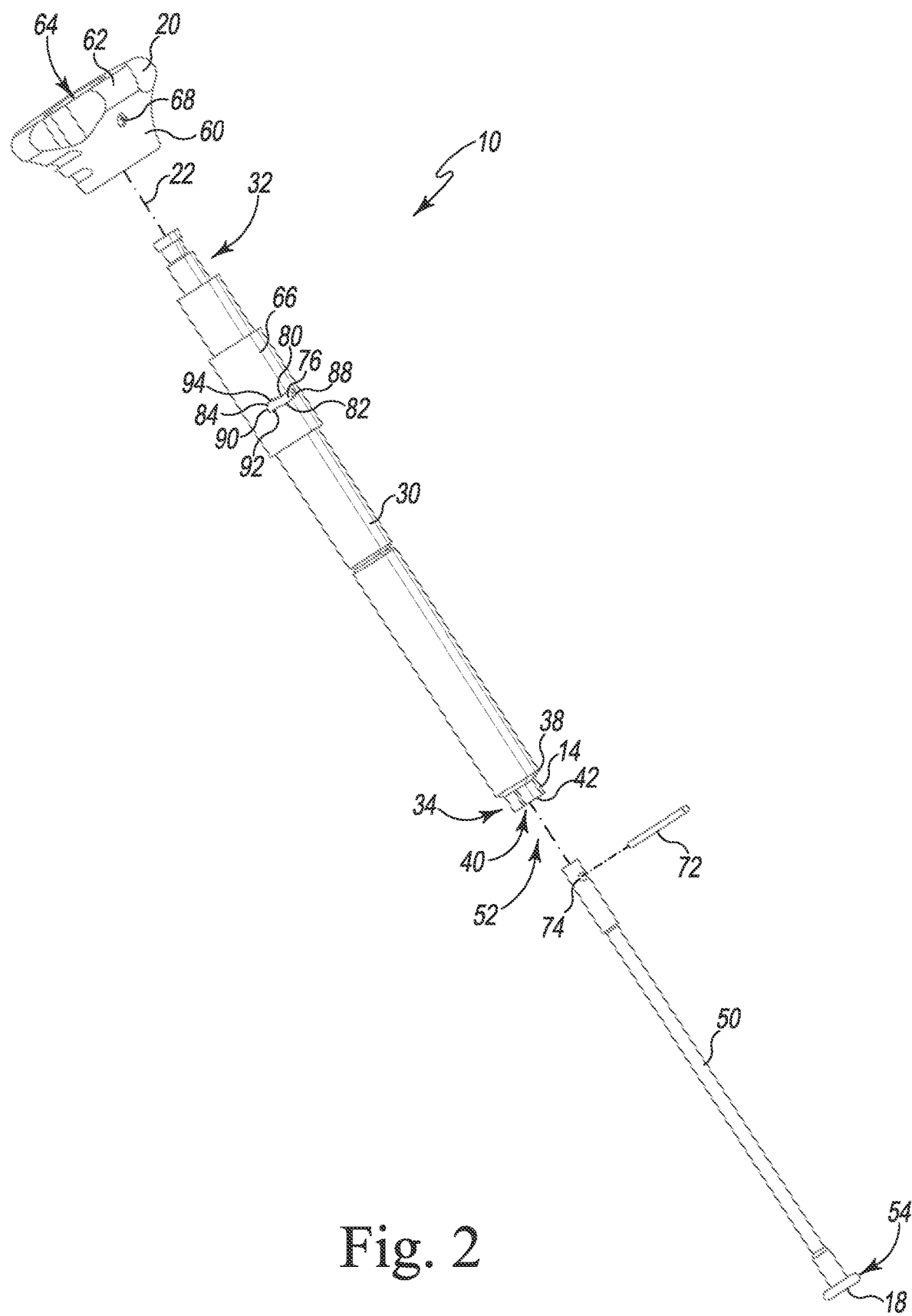
FIG. 2 is an exploded perspective view of the instrument of FIG. 1.

Referring now to FIG. 2, the orthopaedic surgical instrument 10 includes an outer shaft 30 that extends along the axis 22 from a longitudinal end 32 to another longitudinal end 34. The longitudinal end 32 of the outer shaft 30 includes the distal end 24 of the instrument 10, and the longitudinal end 34 includes the instrument head 14, which extends outwardly from a distal wall 38 of the outer shaft 30. In the illustrative embodiment, the outer shaft 30 is a single monolithic component formed from a metallic material such as, for example, stainless steel. It should be appreciated that in other embodiments the outer shaft may be formed from one or more components, which may be formed from different materials. The outer shaft 30 also includes a distal opening 40 that is defined in the head 14, and a cavity 42 extends inwardly from the distal opening 40 to a closed end 44 (see FIG. 3).

The instrument 10 also includes an inner shaft 50 that is sized to be positioned in the cavity 42 of the outer shaft 30. The inner shaft 50 extends along the axis 22 from a longitudinal end 52 that is positioned near the closed end 44 of the cavity 42 to another longitudinal end 54 positioned at the distal opening 40. The inner shaft 50 is configured to operate as a torsion spring and deform and twist about the axis 22. As shown in FIG. 2, the retaining flange 18 is attached to the end 54 of the inner shaft 50. In the illustrative embodiment, the inner shaft 50 and the retaining flange 18 are formed as a single monolithic component from a metallic material such as, for example, stainless steel. It should be appreciated that in other embodiments some or all of the inner shaft 50 and the retaining flange 18 may be formed separately and later assembled. Additionally, the components may be formed from different materials.

The handle 20 of the surgical instrument 10 includes an annular body 60 that is sized to be positioned over the outer shaft 30. In the illustrative embodiment, the annular body 60 is a single monolithic component formed from a metallic material such as, for example, stainless steel. It should be appreciated that in other embodiments the handle may be formed from one or more components, which may be formed from different materials. As shown in FIG. 2, the annular body 60 includes a knurled outer surface 62 configured to be gripped by a hand of a surgeon or other user of the surgical instrument 10. The annular body 60 also includes a central passageway 64 that extends along the axis 22. The central passageway 64 is sized to receive a cylindrical section 66 of the outer shaft 30. The annular body 60 also includes a bore 68 that extends transverse to the longitudinal axis 22 through the knurled outer surface 62 and the central passageway 64. The bore 68 is sized to receive a fastener 72 to secure the handle 20 to the outer and inner shafts 30, 50.

Figure 3:
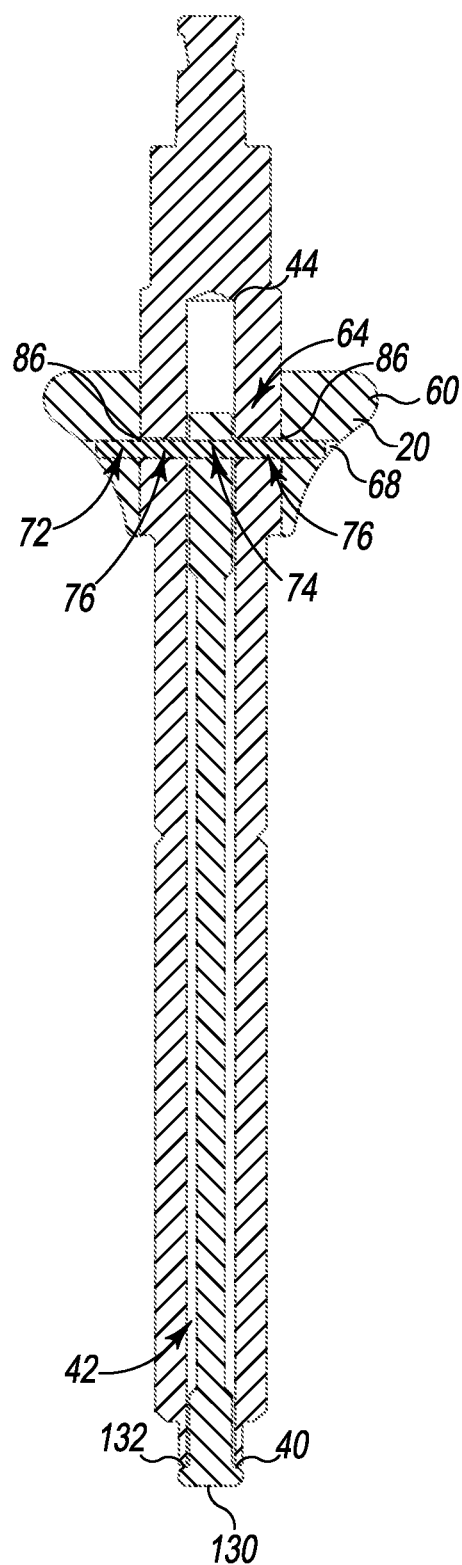
FIG. 3 is a cross-sectional elevation view of the instrument of FIG. 1 taken along line 3-3 of FIG. 1.

The fastener 72 is illustratively a cylindrical shaft sized to be press-fit into the bore 68 and a corresponding bore 74 extending through the inner shaft 50 at its longitudinal end 52. As shown in FIG. 3, the fastener 72 extends through the bore 68, 74 and a pair of slots 76 defined in the outer shaft 30 to couple the handle 20 to the shafts 30, 50.

Returning to FIG. 2, the slots 76 of the outer shaft 30 have identical configurations such that only the slot 76 shown in FIG. 2 will be described in greater detail. Each slot 76 includes an elongated opening 80 that is defined in an outer surface 82 of the cylindrical section 66 of the outer shaft 30. An inner wall 84 extends inwardly from the elongated opening 80 to another opening 86 (see FIG. 3) that opens into the cavity 42. Each inner wall 84 cooperates with the openings 80, 86 to define each slot 76. Each slot 76 extends circumferentially between a pair of closed ends 88, 90. In the illustrative embodiment, a user may grip the knurled surface 62 of the handle 20 rotate the handle about the axis 22. The rotation of the handle 20 causes the fastener 72 to rotate and advance along the slots 76 between the closed ends 88, 90. The rotation of the fastener 72 causes the inner shaft 50 (and hence the retaining flange 18) to also rotate about the axis 22 between the disengaged position and the engagement position.

The orthopaedic surgical instrument 10 also includes a locking mechanism 92 configured to lock the retaining flange 18 in the engagement position. In the illustrative embodiment, the locking mechanism 92 includes a groove 94 that is positioned at the end 90 of each slot 76. As described in greater detail below, each groove 94 is sized to receive and retain the fastener 72 at the end 90 of each slot 76 to lock the retaining flange 18 in the engagement position shown in FIG. 5.

Figure 4:
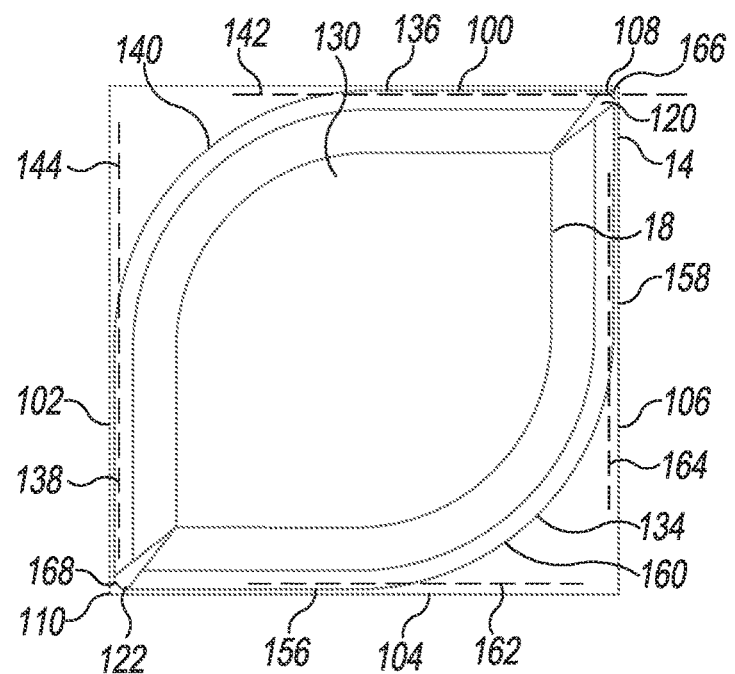
FIG. 4 is a front elevation view of a retaining flange of the orthopaedic surgical instrument of FIG. 1 in one position relative to the head of the orthopaedic surgical instrument of FIG. 1.

Referring now to FIG. 4, the head 14 of the instrument 10 has a square-shaped cross-section. It should be appreciated that in other embodiments the head 14 may take other geometric shapes. In the illustrative embodiment, however, the head 14 includes four planar surfaces 100, 102, 104, 106 that extend from the distal wall 38 and define its square shape. The planar surfaces 100, 106 define a corner 108 on one side of the head 14, while the other planar surfaces 102, 104 define a corner 110 on the opposite side of the head 14.

The retaining flange 18 includes a pair of tips 120, 122 that are configured to be aligned with the head 14 when the retaining flange is located at the disengaged position shown in FIG. 4. Each of the tips 120, 122 is configured to extend beyond the head 14 to engage the medical device 16 when the retaining flange is located at the engagement position, as described in greater detail below. It should be appreciated that in other embodiments the retaining flange may include only a single tip; and still in other embodiments, the retaining flange may include additional tips.

The retaining flange 18 includes a distal surface 130, a proximal surface 132 that faces the longitudinal end 34 of the outer shaft 30, and an outer wall 134 that connects the surfaces 130, 132. As shown in FIG. 4, the outer wall 134 includes a pair of wall segments 136, 138 that are connected by a radius segment 140 to define the outer geometry of the tip 120. The wall segment 136 extends along a substantially straight line 142 that is coincident with the planar surface 100 when the retaining flange 18 is in the disengaged position shown in FIG. 3. As used herein, the term "substantially" refers to tolerance within manufacturing variation. The other wall segment 138 extends along a substantially straight line 144 that is coincident with the planar surface 102 when the retaining flange is in the disengaged position. In that way, the wall segments 136, 138 extend orthogonal to one another in the illustrative embodiment.

The outer wall 134 also includes a pair of wall segments 156, 158 that are connected by a radius segment 160 to define the outer geometry of the other tip 122. The wall segment 156 extends along a substantially straight line 162 that is coincident with the planar surface 104 when the retaining flange 18 is in the disengaged position shown in FIG. 3. The other wall segment 158 extends along a substantially straight line 164 that is coincident with the planar surface 106 when the retaining flange is in the disengaged position. In that way, the wall segments 156, 158 extend orthogonal to one another in the illustrative embodiment.

As shown in FIG. 4, the wall segments 136, 156 extend parallel to each other and are positioned on opposite sides of the retaining flange 18. The wall segments 138, 158 also extend parallel to each other and are positioned on opposite sides of the retaining flange 18. The outer wall 134 includes a curved wall segment 166 that connects the wall segments 136, 158 and another curved wall segment 168 that connects the wall segments 138, 156.

Figure 5:
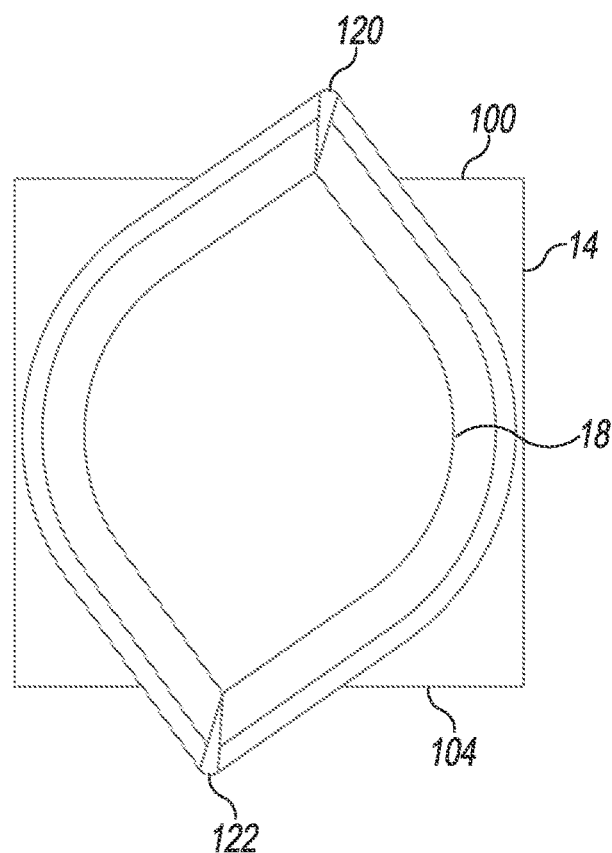
FIG. 5 is a view similar to FIG. 4 showing the retaining flange in another position relative to the head of the orthopaedic surgical instrument.

As shown in FIG. 5, the tips 120, 122 extend beyond the surfaces 100, 104 of the head 14 when the retaining flange 18 is rotated to engagement position. In that position, the tips 120, 122 (including portions of the distal and proximal surfaces 130, 132) are configured to engage corresponding areas of the medical device 16 to secure the medical device 16 to the instrument 10.

The term "medical device" as used herein may refer to an orthopaedic prosthetic component configured to be implanted in a patient's bone or an orthopaedic surgical instrument configured to be used to implant (or plan for the implantation of) an orthopaedic prosthetic component. For example, a medical device may be a femoral prosthetic component, a tibial prosthetic component, a surgical reamer configured to remove tissue to prepare a patient's bone to receive an orthopaedic prosthetic component, or a prosthetic trial component configured to assist the surgeon to select a final orthopaedic prosthetic component.

Figure 6:
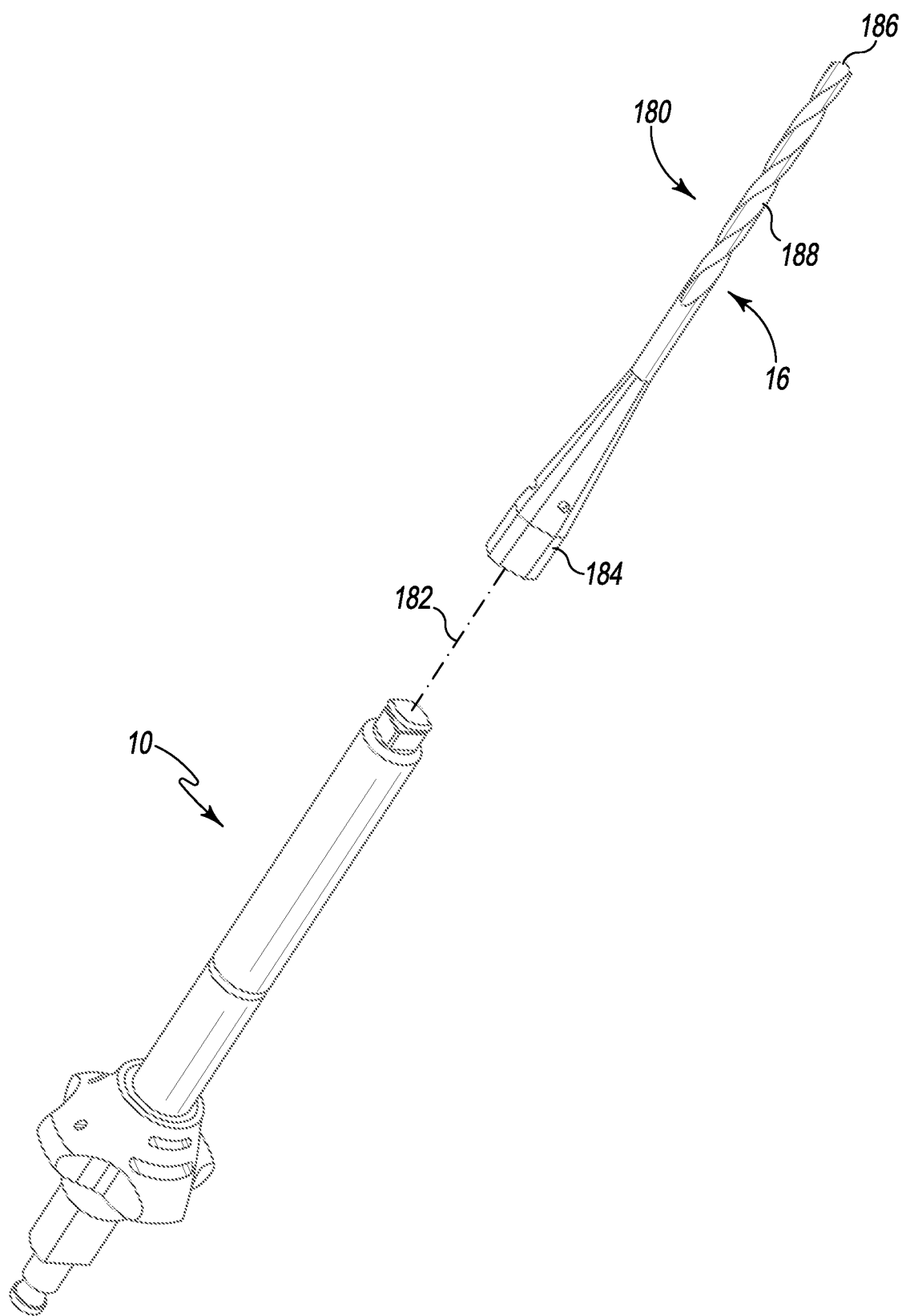
FIG. 6 is a perspective view showing the orthopaedic surgical instrument of FIG. 1 positioned for attachment to a medical device.

Referring now to FIG. 6, the medical device 16 is illustratively embodied as a surgical reamer 180. The reamer 180 extends along a longitudinal axis 182 from a proximal end 184 configured to be coupled to the instrument 10 to a distal end 186. The reamer 180 includes a plurality of cutting teeth 188 at the distal end 186, which are configured to remove tissue to prepare a patient's bone to receive an orthopaedic prosthetic component. In the illustrative embodiment, the reamer 180 is a single monolithic component formed from a metallic material such as, for example, stainless steel. It should be appreciated that in other embodiments the reamer may be formed from one or more components, which may be formed from different materials.

Figure 7:
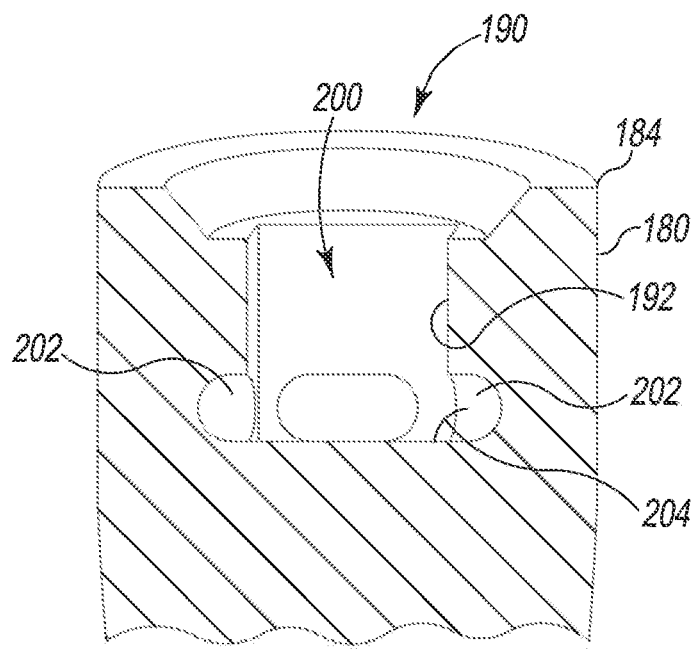
FIG. 7 is a cross-sectional view of an end of the medical device taken along line 7-7 of FIG. 6.
Figure 8:
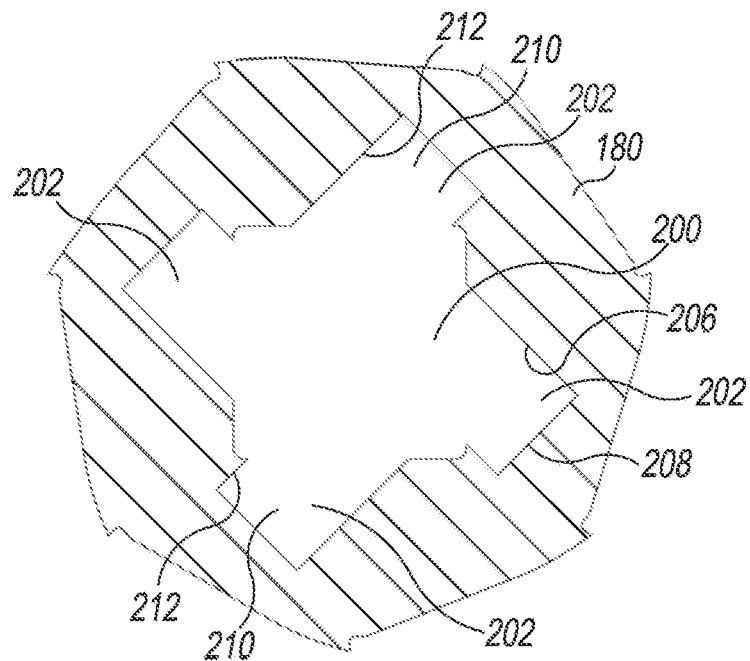
FIG. 8 is a cross-sectional view of the end of the medical device taken along line 8-8 of FIG. 6.

As shown in FIGS. 7 and 8, the reamer 180 includes a proximal opening 190 that is defined in the proximal end 184. A plurality of inner walls 192 extend inwardly from the opening 190 to define a socket 200 sized to receive the head 14 of the surgical instrument 10. In the illustrative embodiment, the socket 200 has a square-shaped cross-section that matches the square-shaped cross-section of the head 14.

The reamer 180 also includes a plurality of apertures 202 that are positioned radially outward from the socket 200. Each aperture 202 includes an opening 204 connected to the socket 200 and a number of inner walls 206 that extends radially outward to a closed end wall 208. The inner walls 206 include an upper wall 210 and side walls 212 that extend from the upper wall 210. The walls 206, 208 and the opening 204 cooperate to define each aperture 202. Each aperture 202 is sized to receive one of the tips 120, 122 of the retaining flange 18. It should be appreciated that in other embodiments the reamer may include fewer apertures and that in such embodiments the retaining flange may include fewer tips.

Figure 9:
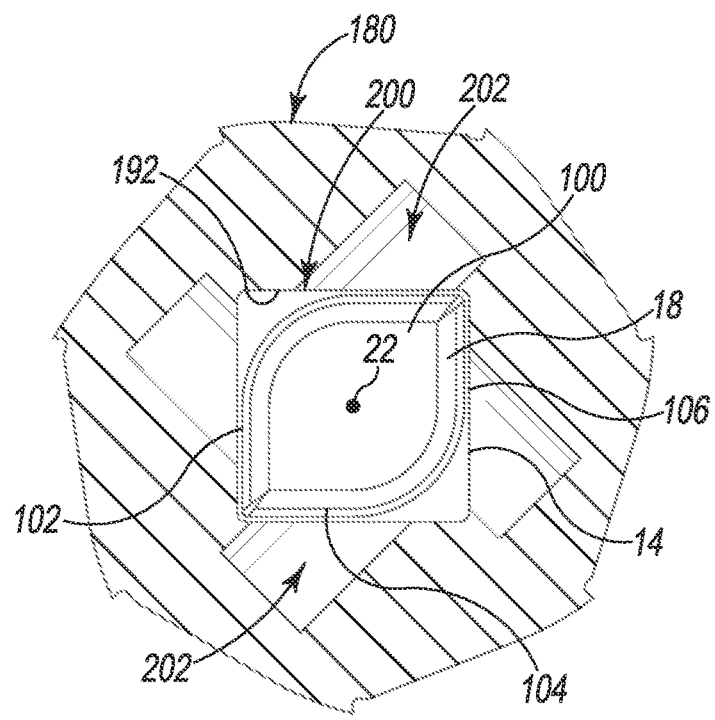
FIG. 9 is a view similar to FIG. 8 showing the retaining flange and the head of the orthopaedic surgical instrument into the medical device of FIG. 6.

In use, a surgeon or other user may align the orthopaedic surgical instrument 10 with the reamer 180 such that their respective longitudinal axes 22, 182 are substantially coincident. With the retaining flange 18 positioned in the disengaged position, the surgeon may advance the head 14 into the socket 200 of the reamer 180. As shown in FIG. 9, the planar surfaces 100, 102, 104, 106 of the head 14 face the inner walls 192 defining the socket 200. The surgeon may continue to advance the head 14 into the socket 200 until the distal wall 38 of the outer shaft 30 engages the proximal end 184 of the surgical reamer 180. When the head 14 is properly positioned in the socket 200, the retaining flange 18 is vertically aligned with the apertures 202 of the surgical reamer 180 and configured for insertion.

Figure 10:
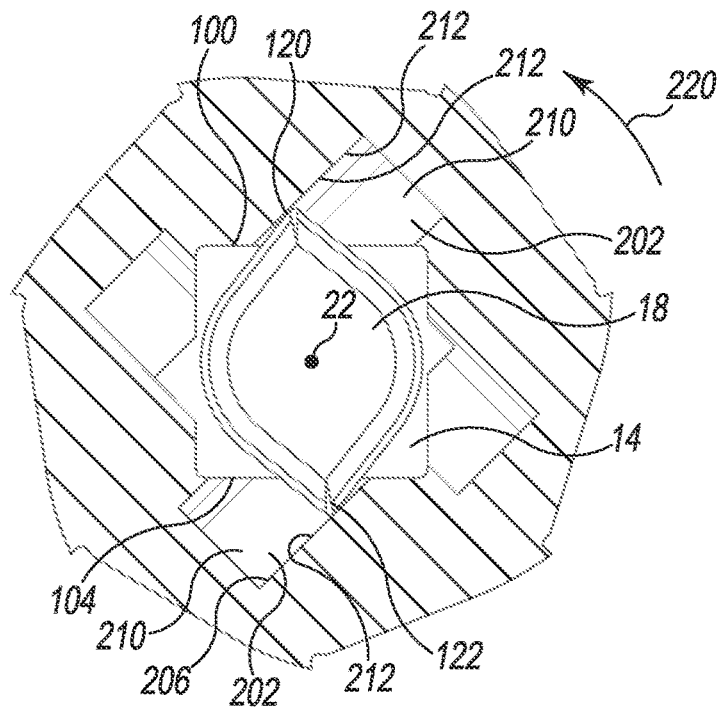
FIG. 10 is a view similar to FIG. 9 showing the retaining flange engaged with the medical device.

The surgeon may grasp the knurled outer surface 62 of the handle 20 and rotate in the direction indicated by arrow 220 in FIG. 10 about the longitudinal axis 22. The rotation of the handle 20 causes the fastener 72 to rotate and advance along the slots 76 between the closed ends 88, 90. The rotation of the fastener 72 causes the inner shaft 50 (and hence the retaining flange 18) to also rotate about the axis 22. As the retaining flange 18 rotates, the tips 120, 122 move out of alignment with the surfaces 100, 104 of the head 14 and advance into two of the apertures 202, as shown in FIG. 10. Each of the tips 120, 122 extends beyond the head 14 and engages the side walls 212 and the upper wall 210 of their respective apertures 202 to secure the reamer 180 to the surgical instrument 10.

With the tips 120, 122 engaging the side walls 212 of the respective aperture 200, the surgeon applies additional torque to the handle 20 to advance the fastener 72 into the groove 94 defined at the end 90 of each elongated slot 76. As torque is applied to the handle 20, the inner shaft 50 is deformed and twisted about the axis 22 to apply a torsion force from the tips 120, 122 of the flange 18 to the side walls 212 of the respective aperture 202. In one embodiment, the inner shaft 50 twists between 10 degrees and 15 degrees. In other embodiments, the inner shaft 50 may twist within other ranges of rotation. As discussed above, the fastener 72 is retained in the groove 94, thereby locking the flange 18 in the engagement position.

With the reamer 180 secured to the surgical instrument 10, the surgeon may connect a rotary power tool to the shank 12 of the surgical instrument 10. The surgeon may then operate the rotary power tool to rotate the instrument 10 and the reamer 180 about their axes 22, 182 to prepare the patient's bone to receive an orthopaedic prosthetic component.

The reamer 180 may be detached from the surgical instrument 10 by rotating the retaining flange 18 in the direction indicated by arrow 222 in FIG. 10. To do so, the surgeon or other user may again grasp the handle 20 and apply sufficient force to advance the fastener 72 out of the groove 94 and along the elongated slot 76 toward the end 88. The rotation of the fastener 72 causes the inner shaft 50 (and hence the retaining flange 18) to also rotate about the axis 22. As the retaining flange 18 rotates, the tips 120, 122 move out of the apertures 202 and back into alignment with the surfaces 100, 104 of the head 14. The surgeon may withdraw the head 14 and the retaining flange 18 from the reamer 180.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. An orthopaedic surgical instrument comprising:
a shaft extending from a first longitudinal end including a head sized to be received in a socket of a medical device and a second longitudinal end including a shank configured to be coupled to a medical instrument,
a retaining flange coupled to the head, the retaining flange being rotatable relative to the head of the shaft between a first position in which a tip of the retaining flange is aligned with the head and a second position in which the tip of the retaining flange extends beyond the head to engage the medical device when the head of the shaft is received in the socket of the medical device, and
a handle configured to be operated by a user to rotate the retaining flange between the first position and the second position,
wherein the tip of the retaining flange is a first tip, and the retaining flange includes a second tip that, when the retaining flange is in the first position, is aligned with the head, and, when the retaining flange is in the second position, extends beyond the head,
wherein (i) the retaining flange includes an outer wall, (ii) the first tip includes a first pair of segments of the outer wall, each segment of the first pair of segments extending along a substantially straight line, and (iii) the second tip includes a second pair of segments of the outer wall, each segment of the second pair of segments extending along a substantially straight line, and
wherein the outer wall includes a pair of curved segments that connect the first pair of segments to the second pair of segments.

2. The orthopaedic surgical instrument of claim 1, wherein:
the head includes a distal edge, and
the tip of the retaining flange includes a section that is sized and shaped to match the distal edge of the head.

3. The orthopaedic surgical instrument of claim 2, wherein:
the distal edge of the head includes a first corner,
the tip section is sized and shaped to match the first corner of the head, and the tip section is aligned with the first corner when the retaining flange is in the first position.

4. The orthopaedic surgical instrument of claim 1, wherein the head of the shaft has a square cross-section.

5. The orthopaedic surgical instrument of claim 1, further comprising:
an inner shaft having a first end positioned adjacent to the first longitudinal end of the shaft and a second end positioned in a cavity defined in the shaft,
wherein the retaining flange is coupled to the second end of the inner shaft.

6. The orthopaedic surgical instrument of claim 5, wherein the handle is coupled to the first end of the inner shaft.

7. The orthopaedic surgical instrument of claim 5, wherein the inner shaft is configured to be twisted about a longitudinal axis extending the first end and the second end to apply a torsion force from the retaining flange to a side wall of the socket.

8. The orthopaedic surgical instrument of claim 1, further comprising a locking mechanism to lock the retaining flange in the second position.

9. The orthopaedic surgical instrument of claim 8, wherein the locking mechanism includes an elongated slot defined in the shaft.

10. An orthopaedic surgical system comprising:
a medical device configured to be inserted into a patient's bone, the medical device including (i) a socket positioned to be accessible to a user when the medical device is positioned in the patient's bone, and (ii) a number of apertures connected to the socket, and
an orthopaedic surgical instrument comprising:
a shaft including a head sized to be received in the socket of the medical device,
a retaining flange coupled to the head, the retaining flange being rotatable relative to the head about an axis between a first position in which a tip of the retaining flange is aligned with the head and a second position in which the tip of the retaining flange is received in one of the number of apertures of the medical device when the head of the shaft is received in the socket of the medical device, and
a handle configured to be operated by the user to rotate the retaining flange between the first position and the second position,
wherein the tip of the retaining flange is a first tip, and the retaining flange includes a second tip that, when the retaining flange is in the first position, is aligned with the head, and, when the retaining flange is in the second position, extends beyond the head,
wherein (i) the retaining flange includes an outer wall, (ii) the first tip includes a first pair of segments of the outer wall, each segment of the first pair of segments extending along a substantially straight line, and (iii) the second tip includes a second pair of segments of the outer wall, each segment of the second pair of segments extending along a substantially straight line, and
wherein the outer wall includes a pair of curved segments that connect the first pair of segments to the second pair of segments.

11. The orthopaedic surgical system of claim 10, wherein:
the head includes a distal edge, and
the tip of the retaining flange includes a section that is sized and shaped to match the distal edge of the head such that, when the retaining flange is positioned in the first position, the head and the retaining flange may be advanced into the socket of the medical device.

12. The orthopaedic surgical system of claim 10, wherein when the retaining flange is in the first position, the second tip is aligned with the head, and, when the retaining flange is in the second position, the second tip is received in another aperture of the number of apertures of the medical device when the head of the shaft is received in the socket of the medical device.

13. The orthopaedic surgical system of claim 10, wherein the shaft includes a shank configured to be coupled to a rotary surgical tool.

* * * * *